United States Patent
Park et al.

(10) Patent No.: US 11,642,050 B2
(45) Date of Patent: *May 9, 2023

(54) APPARATUS AND METHOD FOR ESTIMATING GLUCOSE EXPOSURE AND GENERATING GLUCOSE EXPOSURE ESTIMATION MODEL

(71) Applicant: SAMSUNG ELECTRONICS CO., LTD., Suwon-si (KR)

(72) Inventors: Jin Young Park, Hwaseong-si (KR); Un Jeong Kim, Osan-si (KR); Yun S Park, Suwon-si (KR); Sung Mo Ahn, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 108 days.

This patent is subject to a terminal disclaimer.

(21) Appl. No.: 17/243,063

(22) Filed: Apr. 28, 2021

(65) Prior Publication Data

US 2021/0244321 A1    Aug. 12, 2021

Related U.S. Application Data

(63) Continuation of application No. 16/133,183, filed on Sep. 17, 2018, now Pat. No. 11,020,027.

(30) Foreign Application Priority Data

Sep. 18, 2017    (KR) .................. 10-2017-0119277

(51) Int. Cl.
*A61B 5/1455*    (2006.01)
*A61B 5/145*     (2006.01)
(Continued)

(52) U.S. Cl.
CPC ........ *A61B 5/14532* (2013.01); *A61B 5/0075* (2013.01); *A61B 5/157* (2013.01);
(Continued)

(58) Field of Classification Search
CPC ..... A61B 5/14532; A61B 5/1455; A61B 5/72; A61B 5/7235; A61B 5/7271
See application file for complete search history.

(56) References Cited

U.S. PATENT DOCUMENTS 6,064,897 A    5/2000  Lindberg et al.
6,289,230 B1   9/2001  Chaiken et al.
(Continued)

FOREIGN PATENT DOCUMENTS

CN    104958075 A    10/2015
CN    106604677 A    4/2017
(Continued)

OTHER PUBLICATIONS

Annika M. K. Enejder et al., "Raman Spectroscopy for noninvasive glucose measurements", Journal of Biomedical Optics, vol. 10, No. 3, Jan. 1, 2005, pp. 031114-1-031114-9, XP 055018261. (9 pages total).

(Continued)

*Primary Examiner* — Eric F Winakur
(74) *Attorney, Agent, or Firm* — Sughrue Mion, PLLC

(57) ABSTRACT

An apparatus for estimating a glucose exposure may include: a spectrometer configured to measure a plurality of Raman spectra from an object; and a processor configured to extract depth-specific protein information from the plurality of Raman spectra and estimate the glucose exposure of the object based on the depth-specific protein information.

10 Claims, 13 Drawing Sheets

(51) Int. Cl.
*A61B 5/157* (2006.01)
*A61B 5/00* (2006.01)
*G01N 21/65* (2006.01)

(52) U.S. Cl.
CPC ........... *A61B 5/0064* (2013.01); *A61B 5/0077* (2013.01); *A61B 5/1455* (2013.01); *A61B 5/681* (2013.01); *A61B 5/6898* (2013.01); *G01N 21/65* (2013.01)

(56) References Cited

U.S. PATENT DOCUMENTS

| | | | |
|---|---|---|---|
| 6,487,429 | B2 | 11/2002 | Hockersmith et al. |
| 7,395,158 | B2 | 7/2008 | Monfre et al. |
| 7,430,445 | B2 | 9/2008 | Esenaliev et al. |
| 7,664,605 | B2 | 2/2010 | Chaiken et al. |
| 8,352,005 | B2 | 1/2013 | Esenaliev et al. |
| 8,685,952 | B2 | 4/2014 | Aoki et al. |
| 9,380,942 | B2 | 7/2016 | Henneberg et al. |
| 9,538,943 | B1 | 1/2017 | Cross et al. |
| 9,560,999 | B2 | 2/2017 | Sato et al. |
| 9,924,894 | B2 | 3/2018 | Zhang et al. |
| 10,182,749 | B2 | 1/2019 | Park et al. |
| 10,433,775 | B2 | 10/2019 | Henneberg et al. |
| 10,674,919 | B2 | 6/2020 | Banke |
| 2002/0132279 | A1 | 9/2002 | Hockersmith |
| 2003/0100846 | A1 | 5/2003 | Custer et al. |
| 2003/0144582 | A1 | 7/2003 | Cohen et al. |
| 2003/0208169 | A1 | 11/2003 | Chaiken et al. |
| 2004/0024553 | A1 | 2/2004 | Monfre et al. |
| 2004/0142403 | A1 | 7/2004 | Hetzel et al. |
| 2004/0162678 | A1 | 8/2004 | Hetzel et al. |
| 2004/0197846 | A1 | 10/2004 | Hockersmith et al. |
| 2005/0090750 | A1 | 4/2005 | Ediger et al. |
| 2005/0106651 | A1 | 5/2005 | Chaiken et al. |
| 2006/0195021 | A1 | 8/2006 | Esenal et al. |
| 2007/0049809 | A1 | 3/2007 | Bechtel et al. |
| 2007/0060806 | A1 | 3/2007 | Hunter et al. |
| 2008/0228050 | A1 | 9/2008 | Hwang et al. |
| 2008/0281173 | A1 | 11/2008 | Esenaliev et al. |
| 2008/0316466 | A1 | 12/2008 | Higgins et al. |
| 2009/0079977 | A1 | 3/2009 | Lipson et al. |
| 2009/0098587 | A1 | 4/2009 | Hetzel et al. |
| 2011/0037977 | A1 | 2/2011 | Lipson et al. |
| 2014/0206970 | A1 | 7/2014 | Wesley et al. |
| 2015/0018642 | A1 | 7/2015 | Gulati et al. |
| 2016/0045143 | A1 | 2/2016 | Lee et al. |
| 2016/0061810 | A1 | 3/2016 | Kim et al. |
| 2016/0166187 | A1 | 6/2016 | Pluta et al. |
| 2016/0192867 | A1 | 7/2016 | Esenaliev |
| 2016/0213290 | A1 | 7/2016 | Park et al. |
| 2016/0287154 | A1 | 10/2016 | Chong |
| 2016/0354015 | A1 | 12/2016 | Zhang et al. |
| 2017/0273564 | A1 | 9/2017 | Banke |

FOREIGN PATENT DOCUMENTS

| | | |
|---|---|---|
| EP | 1 094 746 A1 | 5/2001 |
| EP | 1620002 | 2/2006 |
| EP | 1 682 874 | 7/2006 |
| JP | 2004-506610 A | 3/2004 |
| JP | 2004-321325 A | 11/2004 |
| JP | 2007-175242 A | 7/2007 |
| JP | 2010-5047 A | 1/2010 |
| JP | 2013-85650 A | 5/2013 |
| JP | 2013-516256 A | 5/2013 |
| JP | 2017-532541 A | 11/2017 |
| KR | 10-2016-0090579 A | 8/2016 |
| KR | 10-2016-0126502 A | 11/2016 |
| KR | 10-2017-0038351 A | 4/2017 |
| KR | 10-2017-0055409 A | 5/2017 |
| WO | 00/01295 A1 | 1/2000 |
| WO | 2005/047870 A2 | 5/2005 |
| WO | 2007/088705 A1 | 8/2007 |
| WO | 2013/135249 A2 | 9/2013 |
| WO | 2016/034448 A1 | 3/2016 |

OTHER PUBLICATIONS

Search Report dated Feb. 11, 2019 by the European Patent Office in counterpart European Patent Application No. 18194967.8.
Communication dated Mar. 1, 2022 by the Japanese Patent Office in Japanese Patent Application No. 2018-173985.
Communication dated Sep. 28, 2021, issued by the Korean Intellectual Property Office in Korean Patent Application No. 10-2017-0119277.
Xie et al., "Diabetes Diet Nutrition Management Manual", 2017, https://spu.jd.com/12122842.html, 10 pages total.
Communication dated Aug. 24, 2022 by the China National Intellectual Property Administration in Chinese Patent Application No. 201811084445.7.

APPARATUS AND METHOD FOR ESTIMATING GLUCOSE EXPOSURE AND GENERATING GLUCOSE EXPOSURE ESTIMATION MODEL

CROSS-REFERENCE TO RELATED APPLICATION(S)

This is a continuation application of U.S. application Ser. No. 16/133,183, filed Sep. 17, 2018, which claims priority from Korean Patent Application No. 10-2017-0119277, filed on Sep. 18, 2017 in the Korean Intellectual Property Office, the disclosure of which is incorporated herein by reference in its entirety.

BACKGROUND

1. Field

Apparatuses and methods consistent with exemplary embodiments relate to a technology for non-invasively estimating glucose exposure, and more particularly, to estimating glucose exposure using depth-specific protein information based on a Raman spectrum and generating a glucose exposure estimation model for estimating the glucose exposure.

2. Description of Related Art

Protein response in a human body varies depending on a food source. In addition, different types of food are digested at different rates even when the same amounts are ingested. A glycemic index (GI) has been introduced as a way of expressing the rapidity with which a variety of carbohydrate sources are absorbed. The glycemic index is a value given to indicate a quality of carbohydrate by taking into account the rapidity in which the carbohydrate in food is absorbed after meal consumption. The glycemic index of a food may be determined by feeding a group of healthy people a portion of the food containing 50 grams of carbohydrate and then measuring the change in their blood glucose levels over the next 2 hours. A reference value of 100 may be used to represent an equivalent amount of pure glucose.

However, the glycemic index has limitations in taking into account characteristics of each individual (e.g., a degree of response to insulin and a degree of stress) or reflecting their actual dietary lifestyle because glycemic indexes are based on individual foods, but most people eat food in combinations within a meal.

SUMMARY

Exemplary embodiments address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided an apparatus for estimating a glucose exposure, including: a spectrometer configured to measure a plurality of Raman spectra from an object; and a processor configured to extract depth-specific protein information from the plurality of Raman spectra and estimate the glucose exposure of the object based on the depth-specific protein information.

The spectrometer may include a light source configured to emit a light to the object and a photodetector configured to acquire the plurality of Raman spectra by receiving the light reflected or scattered from the object.

The spectrometer may be configured to measure the plurality of Raman spectra at a predetermined time interval for a predetermined period of time.

The processor may be further configured to extract a representative Raman spectrum from the plurality of Raman spectra and extract the depth-specific protein information from the representative Raman spectrum.

The processor may be further configured to extract a median spectrum of the plurality of Raman spectra as the representative Raman spectrum.

The processor may be further configured to extract a Raman spectrum of a predetermined sample number from the plurality of Raman spectra as the representative Raman spectrum.

The processor may be further configured to remove background noise from the extracted representative Raman spectrum.

The depth-specific protein information may include intradermal collagen information and intraepidermal keratin information.

The processor may be further configured to extract a first Raman peak value corresponding to intradermal collagen information and a second Raman peak value corresponding to intraepidermal keratin information from the plurality of Raman spectra and estimate the glucose exposure of the object based on the first Raman peak value, the second Raman peak value, and a glucose exposure estimation model.

The glucose exposure estimation model may define a relationship between the glucose exposure and a ratio of the first Raman peak value to the second Raman peak value.

The processor may be further configured to generate carbohydrate intake guide information based on the glucose exposure of the object.

The carbohydrate intake guide information may include information indicating whether a daily amount of carbohydrate intake of the object is adequate.

The processor may be further configured to calculate a daily amount of the glucose exposure by monitoring the glucose exposure of the object, determine whether the calculated daily amount of the glucose exposure is within a predetermined threshold range, and generate the carbohydrate guide information based on a result of the determination of whether the calculated daily amount is within the predetermined threshold range According to an aspect of another exemplary embodiment, there is provided an apparatus for generating a glucose exposure estimation model, the apparatus including: a data collector configured to collect a Raman spectrum and glucose exposure information corresponding to the Raman spectrum; and a processor configured to extract depth-specific protein information from the Raman spectrum and generate the glucose exposure estimation model based on the depth-specific protein information and the glucose exposure information.

The depth-specific protein information may include intradermal collagen information and intraepidermal keratin information.

The processor may be further configured to extract a first Raman peak value corresponding to intradermal collagen information and a second Raman peak value corresponding to intraepidermal keratin information from the Raman spectrum and generate the glucose exposure estimation model through regression analysis or machine learning based on a ratio of the first Raman peak value to the second Raman peak value and the glucose exposure data.

According to an aspect of another exemplary embodiment, there is provided a method of estimating glucose exposure, the method including: measuring a plurality of Raman spectra from an object; extracting depth-specific protein information from the plurality of Raman spectra; and estimating a glucose exposure of the object based on the depth-specific protein information.

The measuring the plurality of Raman spectra may include measuring the plurality of Raman spectra at a predetermined time interval for a predetermined period of time.

The extracting the depth-specific protein information may include extracting a representative Raman spectrum from the plurality of Raman spectra and extracting the depth-specific protein information from the representative Raman spectrum.

The extracting the representative Raman spectrum may include extracting a median spectrum of the plurality of Raman spectra as the representative Raman spectrum.

The extracting the representative Raman spectrum may include extracting a Raman spectrum of a predetermined sample number from the plurality of Raman spectra as the representative Raman spectrum.

The extracting the depth-specific protein information may further include removing background noise from the extracted representative Raman spectrum.

The depth-specific information may include intradermal collagen information and intraepidermal keratin information.

The extracting the depth-specific protein information may include extracting a first Raman peak value corresponding to intradermal collagen information and a second Raman peak value corresponding to intraepidermal keratin information from the plurality of Raman spectra, and wherein the estimating the glucose exposure of the object may include estimating the glucose exposure of the object using the first Raman peak value, the second Raman peak value, and a glucose exposure estimation model.

The glucose exposure estimation model may define a relationship between the glucose exposure and a ratio of the first Raman peak value to the second Raman peak value.

The method may further include generating carbohydrate intake guide information based on the glucose exposure of the object.

The carbohydrate intake guide information may include information indicating whether a daily amount of carbohydrate intake of the object is adequate.

The generating the carbohydrate intake guide information may include calculating a daily amount of the glucose exposure by monitoring the glucose exposure of the object, determining whether the calculated daily amount of the glucose exposure is within a predetermined threshold range, and generating the carbohydrate intake guide information based on a determination of whether the calculated daily amount of the glucose exposure is within the predetermined threshold range.

According to an aspect of another exemplary embodiment, there is provided an apparatus for measuring a glycemic index, the apparatus comprising: a spectrometer configured to detect an optical spectrum from a subject; a storage configured to store a relationship between a blood glucose area under a curve (AUC) and a ratio of a first reference peak value at a first wavenumber to a second reference peak value at a second wavenumber of a Raman spectrum; and a processor configured to extract a first measurement peak value at the first wavenumber and a second measurement peak value at the second wavenumber of the optical spectrum, and determine the glycemic index of the subject by applying the first measurement peak value and the second measurement peak value to the relationship between the blood glucose AUC and the ratio of the first reference peak value to the second reference peak value.

The first measurement peak value at the first wavenumber and the second measurement peak value at the second wavenumber of the optical spectrum may indicate information of proteins located at different depths from a skin surface of the subject.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
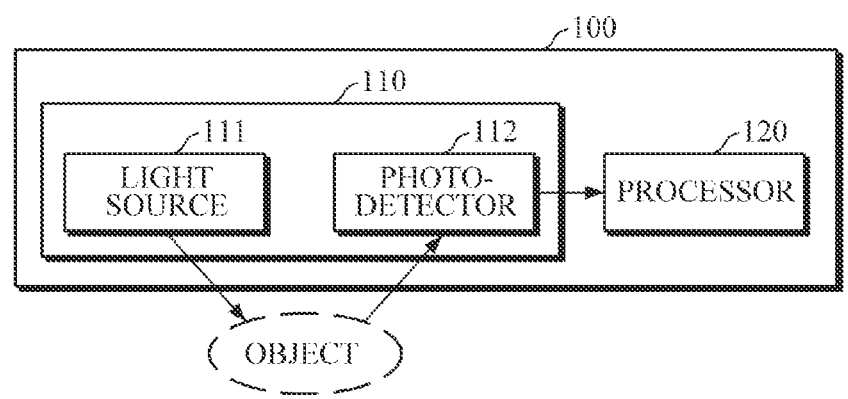
FIG. 1 is a block diagram illustrating an apparatus for estimating glucose exposure according to one exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described in below are selected by considering functions in the embodiment and meanings may vary depending on, for example, a user or operator's intentions or customs. Therefore, in the following embodiments, when terms are specifically defined, the meanings of terms should be interpreted based on definitions, and otherwise, should be interpreted based on general meanings recognized by those skilled in the art.

As used herein, the singular forms are intended to include the plural forms as well, unless the context clearly indicates otherwise. It will be further understood that the terms "comprises" and/or "comprising," or "includes" and/or "including" when used in this description, specify the presence of stated features, numbers, steps, operations, elements, components or combinations thereof, but do not preclude the presence or addition of one or more other features, numbers, steps, operations, elements, components or combinations thereof.

Expressions such as "at least one of," when preceding a list of elements, modify the entire list of elements and do not modify the individual elements of the list.

It will also be understood that the elements or components in the following description are discriminated in accordance with their respective main functions. In other words, two or more elements may be made into one element or one element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

FIG. 1 is a block diagram illustrating an apparatus 100 for estimating glucose exposure according to one exemplary embodiment. The apparatus 100 may estimate glucose exposure using depth-specific protein information based on Raman spectrum, and may be mounted in an electronic device. In particular, the electronic device may include a mobile phone, a smartphone, a tablet computer, a notebook computer, a personal digital assistant (PDA), a portable multimedia player (PMP), a navigation system, an MP3 player, a digital camera, a wearable device, and the like. The wearable device may include a wristwatch type, a wristband type, a ring-type, a belt-type, a necklace type, an ankle-band type, a thigh-band type, a forearm band type, and the like. However, the electronic device and the wearable device are not limited to the above examples.

Referring to FIG. 1, the apparatus 100 includes a spectrometer 110 and a processor 120.

The spectrometer 110 may measure a plurality of Raman spectra from an object. According to one exemplary embodiment, the spectrometer 110 may include a light source 111 and a photodetector 112, and may measure a plurality of Raman spectra at a predetermined time interval for a predetermined period of time by operating the light source 111 and the photodetector 112. For example, the spectrometer 110 may measure a Raman spectrum of the object at intervals of 5 minutes for 2 hours from when the object starts eating.

The light source 111 may emit a light to the object. In particular, the light source 111 may emit a light of a specific wavelength, for example, in a near infrared ray (NIR) range or a mid-infrared ray (MIR) range to the object. However, the wavelength of the light emitted from the light source 111 may vary according to the purpose of measurement or the type of constituent component to be measured. In addition, the light source 111 may configured with a single light emitter, or a plurality of light emitters. The plurality of light-emitters may emit light of different wavelengths or light of the same wavelength. According to one exemplary embodiment, the light source 111 may include, but not limited to, a light emitting diode (LED), a laser diode, or the like, which are merely illustrative examples.

The light source 111 may further include at least one optical element configured to direct the emitted light to a desired position of the object.

The photodetector 112 may acquire a Raman spectrum of the object by receiving light reflected or scattered from the object. According to one exemplary embodiment, the photodetector 112 may include a photo diode, a photo transistor (PTr), a charge-coupled device (CCD), or the like. The photodetector 112 may not be necessarily configured with a single element, and may be configured in the form of an array of a plurality of elements.

The processor 120 may extract depth-specific protein information from a plurality of measured Raman spectra, and estimate glucose exposure of the object based on the extracted depth-specific protein information. In this case, the depth-specific information may include intradermal collagen information and intraepidermal keratin information, and the glucose exposure may be represented as an area under the curve (AUC) of a body glucose concentration graph.

Hereinafter, the processor 120 will be described in more detail with reference to FIG. 2.

Figure 2:
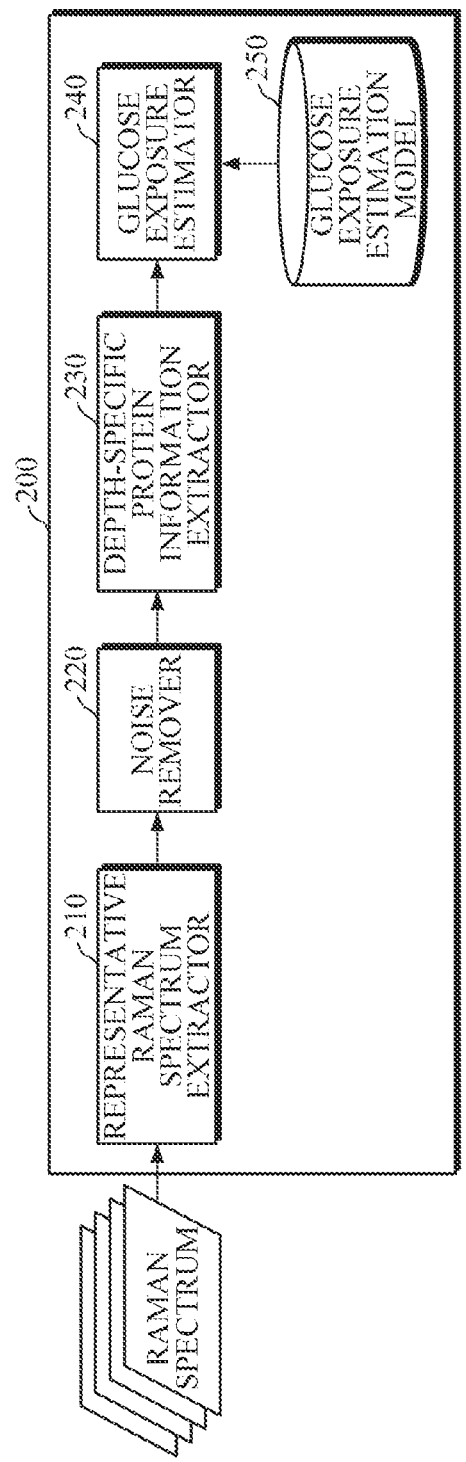
FIG. 2 is a block diagram illustrating a processor according to one exemplary embodiment.

FIG. 2 is a block diagram illustrating a processor according to one exemplary embodiment. The processor 200 of FIG. 2 may be one exemplary embodiment of the processor 120 of FIG. 1.

Referring to FIG. 2, the processor 200 includes a representative Raman spectrum extractor 210, a noise remover 220, a depth-specific protein information extractor 230, and a glucose exposure estimator 240. The processor 200 may further store a glucose exposure estimation model 250 as shown in FIG. 2, but according to another exemplary embodiment, the glucose exposure estimation model 250 may be stored in a memory located outside the processor 200 and may be retrieved from the memory and loaded to the processor 200 to perform an estimation based on the glucose exposure estimation model 250.

The representative Raman spectrum extractor 210 may extract a representative Raman spectrum from a plurality of Raman spectra. According to one exemplary embodiment, the representative Raman spectrum extractor 210 may extract a median spectrum from among the plurality of Raman spectra or a specific Raman spectrum having a predetermined sample number as the representative Raman spectrum. However, these are merely illustrative embodiments, and aspects of the present disclosure are not limited thereto.

The noise remover 220 may remove noise from the extracted representative Raman spectrum.

The Raman spectrum measured from a tissue or cells may include simple additive noise and background noise due to autofluorescence.

According to one exemplary embodiment, the noise remover 220 may remove the simple additive noise from the representative Raman spectrum using a low-band pass filter (e.g., a moving average filter). In addition, the noise remover 220 may estimate a baseline of the representative Raman spectrum and remove the background noise by subtracting the baseline from the representative Raman spectrum. In this case, the baseline may be estimated using a first-order differential method, a rolling ball method, or the like. Here, the first-order differential method uses characteristics of background noise exhibiting a gradual change throughout the entire range. The first-order differential method is a method to estimate a baseline by differentiating a spectrum, finding a significant peak, cutting out the corresponding peak area, and performing interpolation. In addition, the rolling ball method is a method of considering a trace of a highest point of a hypothetical ball that rolls underneath a spectrum as a baseline.

The depth-specific protein information extractor 230 may extract depth-specific protein information from the representative Raman spectrum. In this case, the depth-specific protein information may include intradermal collagen information and intraepidermal keratin information.

A light that is reflected from a subject may carry information about collagen in a dermal layer of the subject (hereinafter, referred to as "intradermal collagen information") and information of keratin in an epidermal layer of the subject (hereinafter, referred to as "intraepidermal keratin information"). According to one exemplary embodiment, the depth-specific protein information extractor 230 may extract a Raman peak value (hereinafter, referred to as a "first Raman peak value") of a first wave number (e.g., 1246 $cm^{-1}$) in the representative Raman spectrum as the intradermal collagen information and extract a Raman peak value (hereinafter, referred to as a "second Raman peak value") of a second wave number (e.g., 1650 $cm^{-1}$) as the intraepidermal keratin information. In this case, the first wave number is related to the intradermal collagen information, the second wave number is related to the intraepidermal keratin information, and information on the first and second wave numbers is experimentally derived in advance and stored in an internal or external database.

The glucose exposure estimator 240 may estimate the glucose exposure of the object using the depth-specific protein information.

For example, the glucose exposure estimator 240 may determine a ratio of the first Raman peak value and the second Raman peak value and estimate the glucose exposure of the object using the ratio of the first Raman peak value and the second Raman peak value and the glucose exposure estimation model 250. In particular, the glucose exposure estimation model 250 defines a relationship between the ratio of the first Raman peak value and the second Raman peak value and the glucose exposure, and may be stored in a database inside or outside the processor 200.

Figure 3:
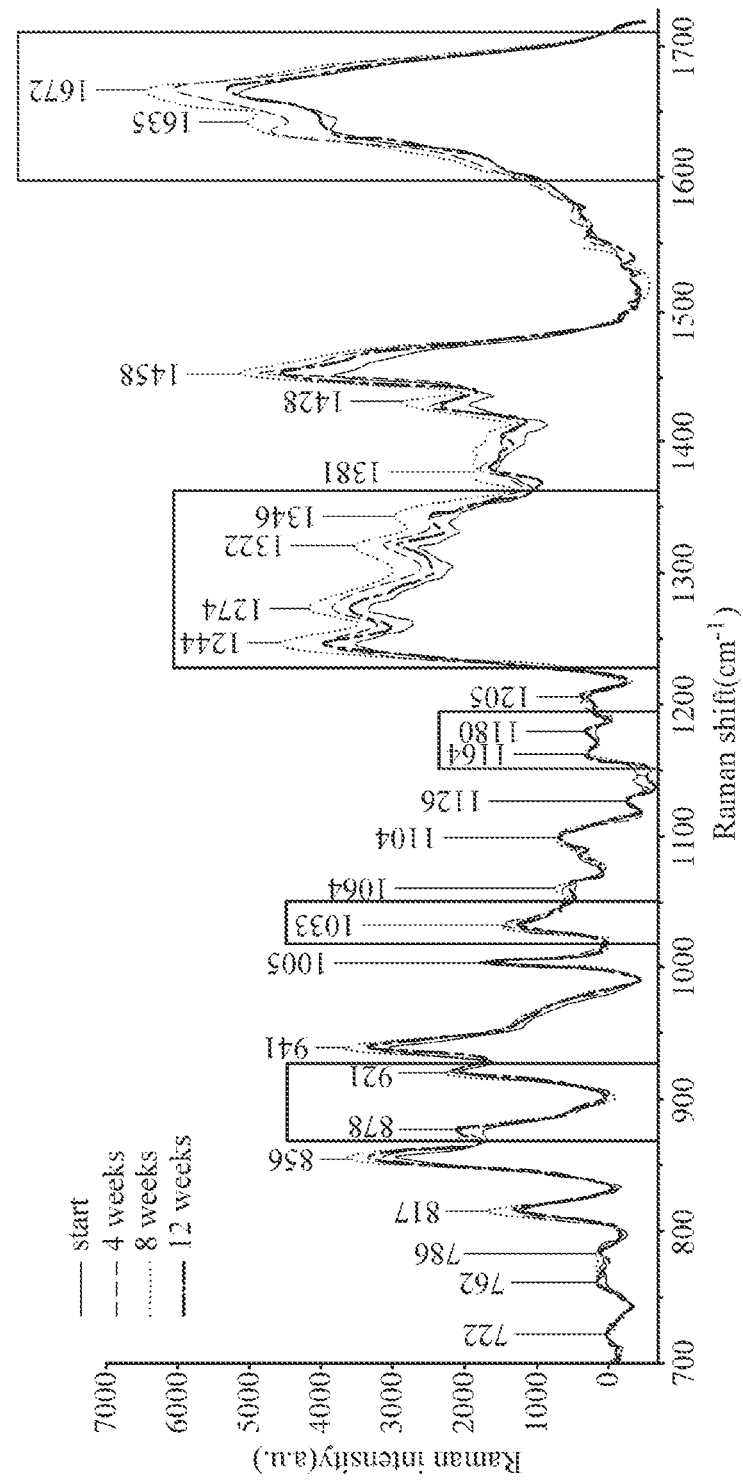
FIG. 3 is a graph for describing a relationship between Raman peak shift corresponding to intradermal collagen and glucose exposure.

FIG. 3 is a graph for describing a relationship between Raman peak shift corresponding to intradermal collagen and glucose exposure. More specifically, FIG. 3 shows a Raman peak shift corresponding to the intradermal collagen when a predetermined amount of glucose is continuously fed to a non-human animal. The Raman peak shift may be obtained by emitting a light to the non-human animal and then collecting the light when it is reflected from the non-human animal.

Referring to FIG. 3, a Raman peak at a specific wave number (e.g., a region indicated by a leftmost box in FIG. 3) changes over time while the predetermined amount of glucose is continuously fed to the non-human animal. Therefore, the apparatus 100 for estimating glucose exposure according to one exemplary embodiment may extract depth-specific protein information from the Raman spectrum using such a characteristic and estimate the glucose exposure using the extracted depth-specific protein information.

Figure 4:
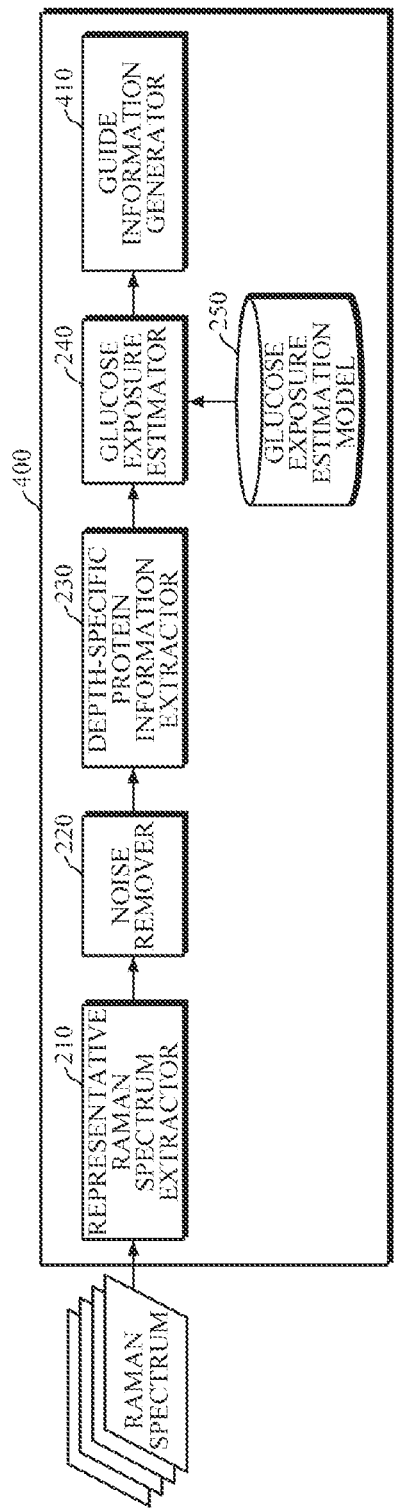
FIG. 4 is a block diagram illustrating a processor according to another exemplary embodiment.

FIG. 4 is a block diagram illustrating a processor according to another exemplary embodiment of the present disclosure. A processor 400 of FIG. 4 may be another exemplary embodiment of the processor 120 of FIG. 1.

Referring to FIG. 4, the processor 400 includes a representative Raman spectrum extractor 210, a noise remover 220, a depth-specific protein information extractor 230, a glucose exposure estimator 240, and a guide information generator 410. The processor 400 may further store the glucose exposure estimation model 250 as shown in FIG. 4, but according to another exemplary embodiment, the glucose exposure estimation model 250 may be stored in a memory located outside the processor 400 and may be retrieved from the memory and loaded to the processor 400 to perform an estimation based on the glucose exposure estimation model 250.

In this case, the representative Raman spectrum extractor 210, the noise remover 220, the depth-specific protein information extractor 230, and the glucose exposure estimator 240 may be substantially the same as those described with reference to FIG. 2, and thus detailed descriptions thereof will not be reiterated.

The guide information generator 410 may generate carbohydrate intake guide information that indicates whether a daily amount of carbohydrate intake of the object is adequate by using the glucose exposure of the object.

For example, the guide information generator 410 may monitor the glucose exposure of the object to calculate daily glucose exposure and determine whether the calculated daily glucose exposure falls within a predetermined threshold range. In addition, when the daily glucose exposure is within the predetermined threshold range, the guide information generator 410 may determine that a carbohydrate intake amount is adequate. When the daily glucose exposure is less than the predetermined threshold range, the guide information generator 410 may determine that the daily amount of carbohydrate intake is insufficient, and when the daily glucose exposure is greater than the predetermined threshold range, the guide information generator 410 may determine that the daily amount of carbohydrate intake is excessive. The guide information generator 410 may generate carbohydrate intake guide information that indicates whether or not the daily amount of carbohydrate intake of the object is adequate based on the determination.

In this case, the predetermined threshold range may be derived through the following procedures in advance and stored in a database inside or outside the processor 400.

Step 1: An object takes a reference food and a first glucose exposure is measured. For example, the first glucose exposure X (unit: mg·min/dL) is measured when the object takes an amount K of reference food (unit: grams (g)). Specifically, the processor 200, 400 may generate a two-hour blood glucose response curve by monitoring a blood sugar level of the object for two hours since the object consumes the K amount of the reference food. The processor 200, 400 may calculate an area under the curve (AUC) as the first glucose exposure X.

Step 2: A second glucose exposure corresponding to a recommended daily amount of carbohydrate intake is calculated. For example, when a recommended daily amount of carbohydrate intake is A (unit: g), the second glucose exposure R corresponding to the recommended daily amount A of carbohydrate is calculated based on the following equation:

$$(A*X)/K=R \text{ (unit: mg·min/dL)}.$$

Step 3: A third glucose exposure incurring when all the recommended daily calories are obtained only from carbohydrates is calculated. For example, when recommended daily calories are B (unit: kcal), the third glucose exposure T incurring when all the recommended daily calories B are obtained only from carbohydrates is calculated based on the following equation:

$$(B*X)/(K*4)=T \text{ (unit: mg·min/dL)}.$$

Step 4: The third glucose exposure is assumed as a maximum amount of carbohydrate intake, and a predetermined range from the glucose exposure corresponding to the recommended daily amount of carbohydrate intake is set to be in a predetermined threshold range. For example, the predetermined threshold range may be R−α to R+β. In this case, α may be variously set as a positive number less than R and β may be variously set as a positive number less than T−R.

Figure 5:
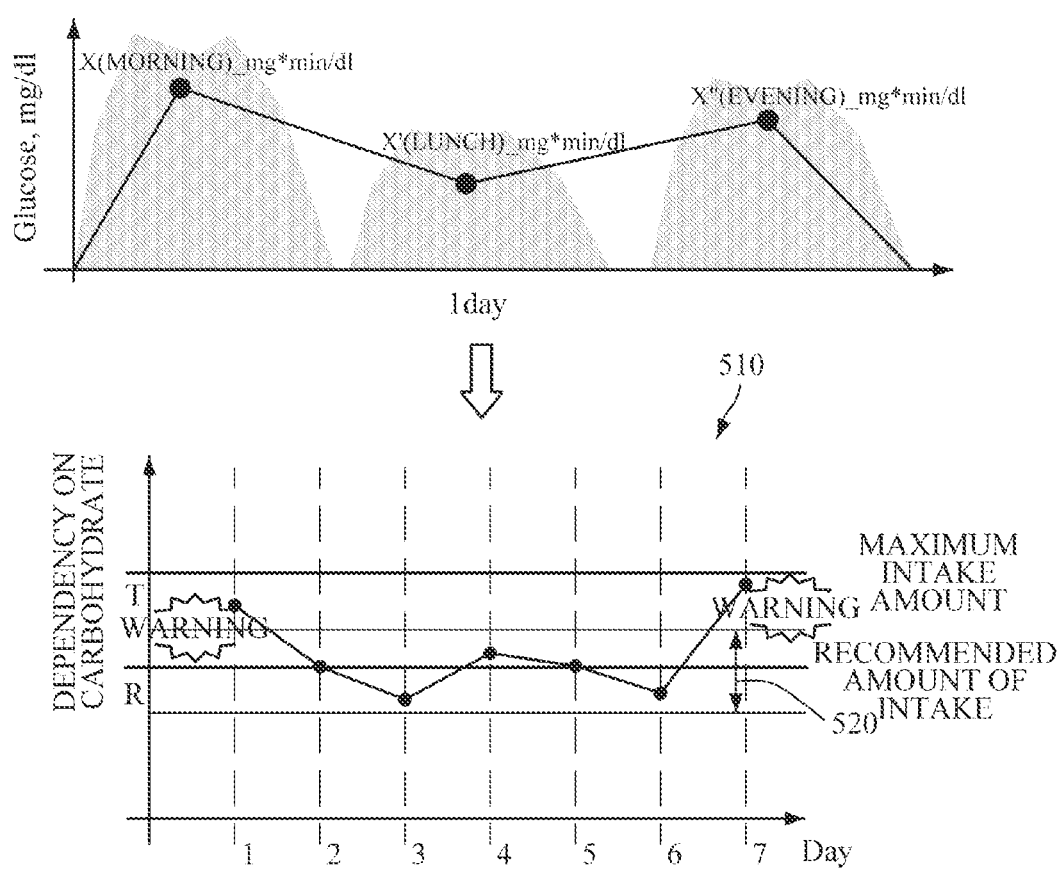
FIG. 5 shows graphs illustrating an example of carbohydrate intake guide information.

FIG. 5 shows graphs illustrating an example of carbohydrate intake guide information.

Referring to FIGS. 4 and 5, the guide information generator 410 may calculate a daily glucose exposure based on glucose exposure estimated at breakfast time, lunch time, and dinner time, determine whether the calculated daily glucose exposure is within a predetermined threshold range 520 of a recommended amount of glucose intake, and generate carbohydrate intake guide information 510 based on the determination of whether the calculated daily glucose exposure is within the predetermined threshold range 520.

In the example shown in FIG. 5, in which the daily glucose exposure on the first day and the seventh day is out of the predetermined threshold range 520, the guide information generator 410 may determine that carbohydrate intake on the first day and the seventh day is excessive, and hence may generate various warning messages.

Figure 6:
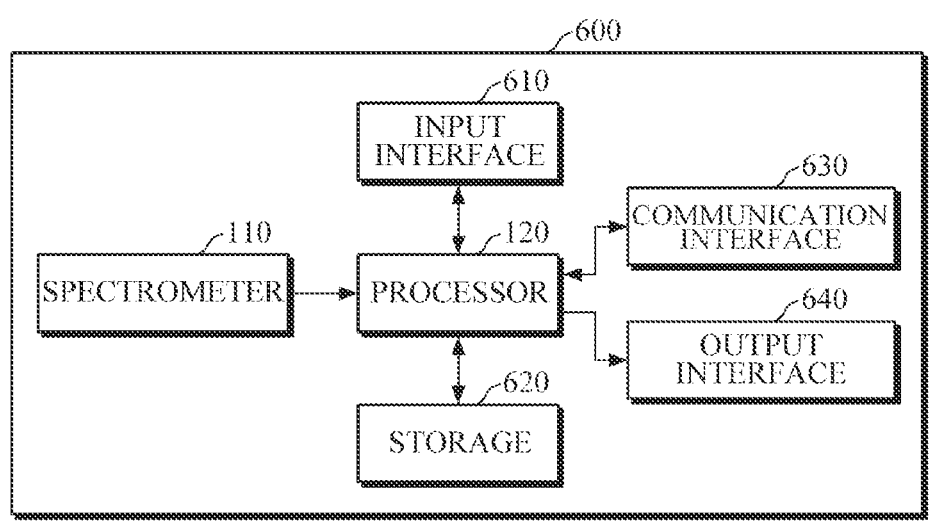
FIG. 6 is a block diagram illustrating an apparatus for estimating glucose exposure according to another exemplary embodiment.

FIG. 6 is a block diagram illustrating an apparatus 600 for estimating glucose exposure according to another exemplary embodiment. The apparatus 600 may estimate the amount of glucose exposure using depth-specific protein information based on a Raman spectrum. The apparatus 600 may be mounted in an electronic device, for example, such as a mobile phone, a smartphone, a tablet computer, a notebook computer, a PDA, a PMP, a navigation system, an MP3 player, a digital camera, a wearable device, and the like. The wearable device may include a wristwatch type, a wristband type, a ring-type, a belt-type, a necklace type, an ankle-band type, a thigh-band type, a forearm band type, and the like. However, the electronic device and the wearable device are not limited to the above examples.

Referring to FIG. 6, the apparatus 600 includes a spectrometer 110, a processor 120, an input interface 610, a storage 620, a communication interface 630, and an output interface 640. In this case, the spectrometer 110 and the processor 120 may perform substantially the same operations as those described with reference to FIGS. 1 to 4, and hence detailed descriptions thereof will not be reiterated.

The input interface 610 may receive various operation signals from a user. According to one exemplary embodiment, the input interface 610 may include a keypad, a dome switch, a resistive or capacitive touch pad, a jog wheel, a jog switch, a hardware button, and the like. In particular, when a touch pad has a layered structure with a display, this structure may be referred to as a touch screen.

Programs or instructions for operations of the apparatus 600 may be stored in the storage 620 and data input to and output from the apparatus 600 may also be stored in the storage 620. In addition, a plurality of pieces of Raman spectrum data measured by the spectrometer 110, representative Raman spectrum data extracted by the processor 120, depth-specific protein information extracted by the processor 120, glucose exposure estimate data obtained by the processor 120, carbohydrate intake guide information generated by the processor 120, and a glucose exposure estimation model, and the like may be stored in the storage 620.

The storage may include at least one type of storage media, such as a flash memory, a hard disk type memory, a multimedia card micro type memory, a card-type memory (e.g., SD or XD memory), random access memory (RAM), static random access memory (SRAM), read only memory (ROM), electrically erasable programmable read only memory (EEPROM), programmable read only memory (PROM), magnetic memory, and optical disk. In addition, the apparatus 600 may operate an external storage medium, such as web storage providing a storage function of the storage 620.

The communication interface 630 may communicate with an external device. For example, the communication interface 630 may transmit the data input from the user through the input interface 610, the plurality of pieces of Raman spectrum data measured by the spectrometer 110, the representative Raman spectrum data extracted by the processor 120, the depth-specific protein information extracted by the processor 120, the glucose exposure estimate data obtained by the processor 120, the carbohydrate intake guide information generated by the processor 120, and the glucose exposure estimation model to the external device, or may receive a variety of data to estimate the glucose exposure or generating the carbohydrate guide information from the external device.

In this case, the external device may be a medical device that uses the plurality of pieces of Raman spectrum data measured by the spectrometer 110, the representative Raman spectrum data extracted by the processor 120, the depth-specific protein information extracted by the processor 120, the glucose exposure estimate data obtained by the processor 120, the carbohydrate intake guide information generated by the processor 120, or the glucose exposure estimation model, or a printer or a display device to output a result. In addition, the external device may be a digital TV, a desktop computer, a mobile phone, a smartphone, a tablet computer, a notebook computer, a PDA, a PMP, a navigation system, an MP3 player, a digital camera, a wearable device, or the like, but is not limited thereto.

The communication interface 630 may communicate with the external device through various communication schemes, such as Bluetooth communication, Bluetooth low energy communication, near field communication (NFC), wireless local area network (WLAN) communication, ZigBee communication, infrared data association (IrDA) communication, radio frequency identification communication, $3^{rd}$ generation (3G) communication, 4G communication, 5G communication, and the like. However, these are merely examples, and the communication scheme is not limited thereto.

The output interface 640 may output the plurality of pieces of Raman spectrum data measured by the spectrometer 110, the representative Raman spectrum data extracted by the processor 120, the depth-specific protein information extracted by the processor 120, the glucose exposure estimate data obtained by the processor 120, the carbohydrate intake guide information generated by the processor 120, or the glucose exposure estimation model. According to one exemplary embodiment, the output interface 640 may output the plurality of pieces of Raman spectrum data measured by the spectrometer 110, the representative Raman spectrum data extracted by the processor 120, the depth-specific protein information extracted by the processor 120, the glucose exposure estimate data obtained by the processor 120, the carbohydrate intake guide information generated by the processor 120, or the glucose exposure estimation model in at least one of visual, audible, and tactile manners. To this end, the output interface 640 may include a display, a speaker, a vibrator, and the like.

Figure 7:
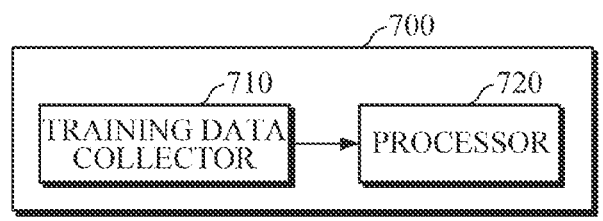
FIG. 7 is a block diagram illustrating an apparatus for generating a glucose exposure estimation model according to one exemplary embodiment.

FIG. 7 is a block diagram illustrating an apparatus 700 for generating a glucose exposure estimation model according to one exemplary embodiment. The apparatus 700 may estimate a glucose exposure estimation model to be used in the apparatus 100 of FIG. 1 and/or the apparatus of FIG. 6 for estimating glucose exposure, and may be mounted in an electronic device. In this case, the electronic device may include a mobile phone, a smartphone, a tablet computer, a notebook computer, a PDA, a PMP, a navigation system, an MP3 player, a digital camera, a wearable device, and the like. The wearable device may include a wristwatch type, a wristband type, a ring-type, a belt-type, a necklace type, an ankle-band type, a thigh-band type, a forearm band type, and the like. However, the electronic device and the wearable device are not limited to the above examples.

As shown in FIG. 7, the apparatus 700 may include a training data collector 710 and a processor 720.

The training data collector 710 may collect a Raman spectrum and glucose exposure information corresponding to the Raman spectrum as training data. In particular, the Raman spectrum collected as the training data may be a plurality of Raman spectra measured at a predetermined time interval for a predetermined period of time, or a representative Raman spectrum extracted from the plurality of Raman spectra. In addition, the Raman spectrum collected as the training data may be raw data from which noise has not been removed or data from which noise has removed.

The processor 720 may obtain depth-specific protein information from the collected Raman spectrum and may generate a glucose exposure estimation model based on the extracted depth-specific protein information and glucose exposure data corresponding to the Raman spectrum. The processor 720 may obtain the glucose exposure data by calculating an area under a blood glucose response curve that is measured for two hours since food is consumed. The depth-specific protein information may include intradermal collagen information and intraepidermal keratin information.

For example, the processor 720 may extract a first Raman peak value from the Raman spectrum as the intradermal collagen information and extract a second Raman peak value as the intraepidermal keratin information. In addition, the processor 720 may calculate a ratio of the first Raman peak value and the second Raman peak value and generate the glucose exposure estimation model through regression analysis or machine learning using the ratio of the first Raman peak value and the second Raman peak value and the corresponding glucose exposure information. In this case, a regression analysis algorithm may include a simple linear regression algorithm, a multi-linear regression algorithm, a logistic regression algorithm, a proportional Cox regression algorithm, and the like, and a machine learning algorithm may include an artificial neural network algorithm, a decision tree algorithm, a genetic algorithm, a genetic programming algorithm, a K-nearest neighbor algorithm, a radial basis function network algorithm, a random forest algorithm, a support vector machine algorithm, and a deep learning algorithm.

Meanwhile, the processor 720 may perform various pre-processing operations according to the Raman spectrum collected by the training data collector 710. For example, when the collected Raman spectrum is raw data, the processor may remove simple additive noise and/or background noise from the collected Raman spectrum. In addition, when the collected Raman spectrum data is a plurality of Raman spectra measured at a predetermined time interval for a predetermined period of time, the processor 720 may extract a representative Raman spectrum from the plurality of Raman spectra.

In this case, a method of removing noise and a method of extracting a spectrum are substantially the same as those described with reference to FIG. 2, and hence detailed descriptions thereof will not be reiterated.

Figure 8:
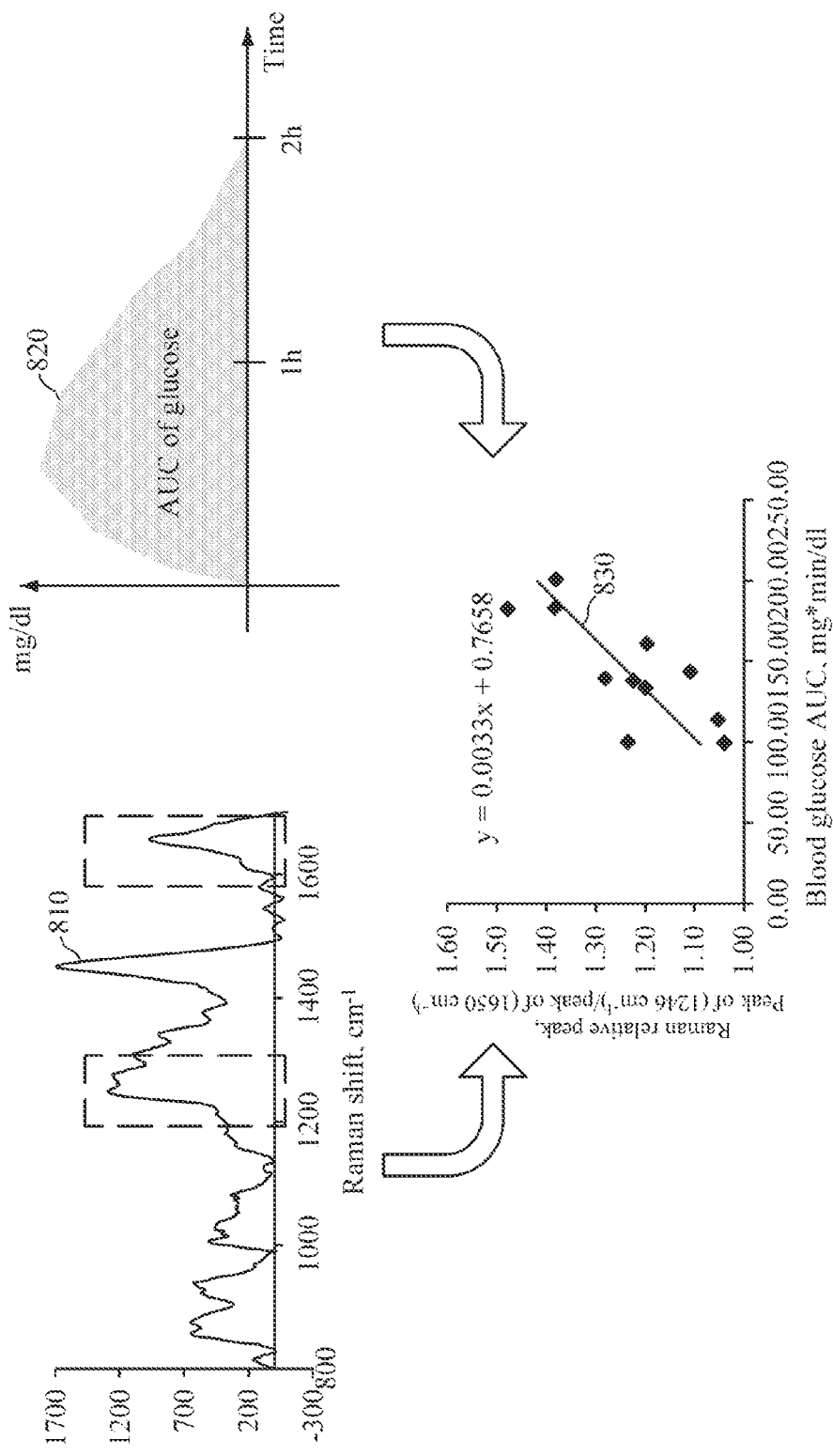
FIG. 8 shows graphs for describing a glucose exposure estimation model generation process.

FIG. 8 shows graphs for describing a glucose exposure estimation model generation process. In FIG. 8, it is assumed that a Raman spectrum collected as training data is a representative Raman spectrum extracted from a plurality of Raman spectra measured at a predetermined time interval for a predetermined period of time and all the noise is removed therefrom.

With reference to FIG. 8, a Raman spectrum 810 may show a change in a collagen peak value according to an amount of glucose exposure. In the Raman spectrum 810, Amide I and Amide III bands may be observed at approximately 1,650 and 1,246 $cm^{-1}$. The measured Amide I band may reflect alpha-helix structure found in epidermal keratin, and the measured Amide III may reflect components in a dermal layer.

Referring to FIGS. 7 and 8, the processor 720 extracts a first Raman peak value (e.g., a Raman peak value at 1246 $cm^{-1}$) from a Raman spectrum 810 as intradermal collagen information and extracts a second Raman peak value (e.g., a Raman peak value at 1650 $cm^{-1}$) as intraepidermal keratin information. The processor 720 calculates a ratio of the first Raman peak value to the second Raman peak value, and calculates an area under a two-hour blood glucose response curve, as a corresponding glucose exposure 820. In turn, the processor 720 generates a glucose exposure estimation model 830 by performing a regression analysis of the ratio of the first Raman peak value to the second Raman peak value and the corresponding glucose exposure 820.

With reference to FIGS. 6 and 8, the storage 620 may store a glucose exposure estimation model that indicates a relationship between an area under the curve (AUC) of a blood glucose graph (e.g., the glucose exposure 820) and the ratio of the first Raman peak value at wavenumber 1246 $cm^{-1}$ to the second Raman peak value at 1650 $cm^{-1}$ of the Raman spectrum 810. When the spectrometer 110 detects an optical spectrum, the processor 120 may detect a first measurement peak value and a second measurement peak value at wavenumber 1246 $cm^{-1}$ and wavenumber 1650 $cm^{-1}$ of the detected optical spectrum, respectively, and may apply the first measurement peak value and the second measurement peak to the glucose exposure estimation model to determine a glycemic index.

Figure 9:
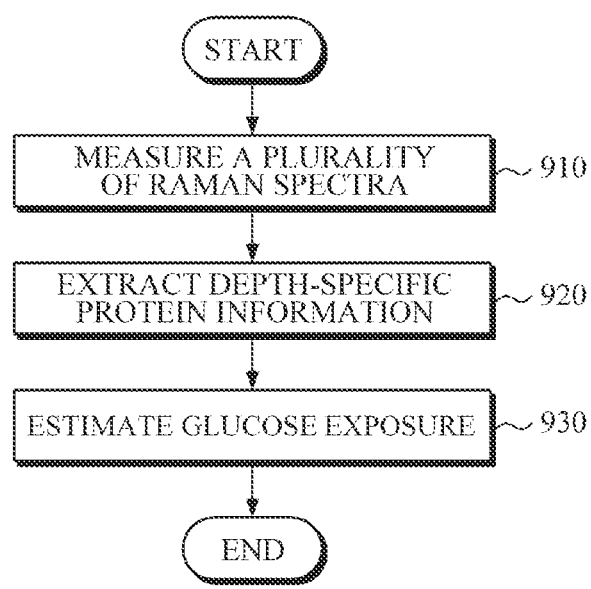
FIG. 9 is a flowchart illustrating a method of estimating glucose exposure according to one exemplary embodiment.

FIG. 9 is a flowchart illustrating a method of estimating glucose exposure according to one exemplary embodiment of the present disclosure. The method of FIG. 9 may be performed by the apparatus 100 of FIG. 1 for estimating glucose exposure.

Referring to FIGS. 1 and 9, the apparatus 100 for estimating glucose exposure measures a plurality of Raman spectra from the object in operation 910. For example, the apparatus 100 may measure the plurality of Raman spectrum by emitting light to the object at a predetermined time interval for a predetermined period of time and receiving light reflected or scattered from the object. In this case, the apparatus 100 may emit light of a specific wavelength, for example, in an NIR range or an MIR range to the object, but aspects of the present disclosure are not limited thereto.

The apparatus 100 extracts depth-specific protein information from the plurality of measured Raman spectra in operation 920. In this case, the depth-specific protein information may include intradermal collagen information and intraepidermal keratin information. For example, the apparatus 100 may extract a first Raman peak value related to the intradermal collagen information and a second Raman peak value related to the intraepidermal keratin information from the plurality of Raman spectra.

The apparatus 100 estimates glucose exposure of the object using the extracted depth-specific protein information in operation 930. For example, the apparatus 100 may estimate the glucose exposure of the object using the first Raman peak value, the second Raman peak value, and a glucose exposure estimation model. In this case, the glucose exposure estimation model may define a relationship between a ratio of the first Raman peak value and the second Raman peak value and the glucose exposure.

Figure 10:
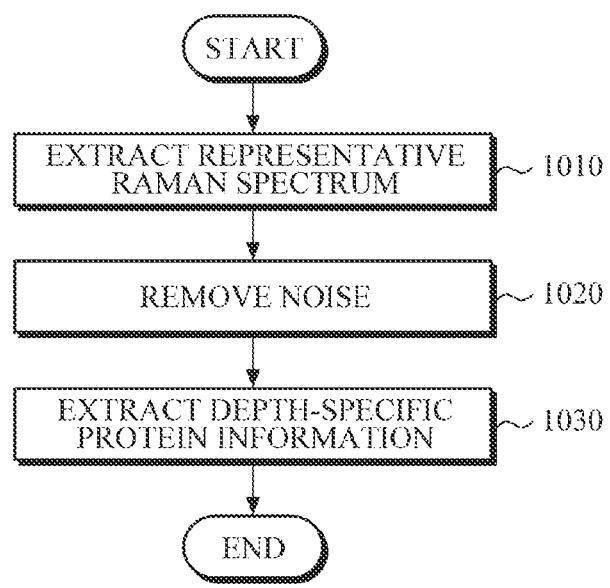
FIG. 10 is a flowchart illustrating a method of extracting depth-specific protein information according to one exemplary embodiment.

FIG. 10 is a flowchart illustrating a method of extracting depth-specific protein information according to one exemplary embodiment. The method of FIG. 10 may be one exemplary embodiment of the operation 920 for extracting depth-specific protein information shown in FIG. 9.

Referring to FIGS. 1 and 10, the apparatus 100 for estimating glucose exposure extracts a representative Raman spectrum from a plurality of Raman spectra in operation 1010. For example, the apparatus 100 may extract a median spectrum of the plurality of Raman spectra as the representative Raman spectrum, or extract a Raman spectrum of a predetermined sample number as the representative Raman spectrum.

The apparatus 100 remove noise from the extracted representative Raman spectrum in operation 1020. For example, the apparatus 100 may remove simple additive noise from the representative Raman spectrum using a low-band pass filter, or may remove noise by estimating a baseline of the representative Raman spectrum and subtracting the estimated baseline from the representative Raman spectrum.

The apparatus 100 extracts depth-specific protein information from the representative Raman spectrum in operation 1030. For example, the apparatus 100 may extract a first Raman peak value related to intradermal collagen information and a second Raman peak value related to intraepidermal keratin information from the representative Raman spectrum.

Figure 11:
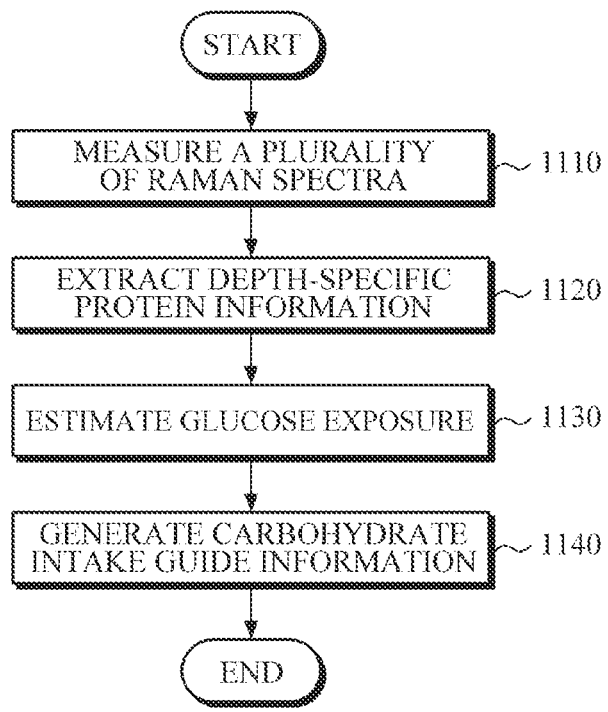
FIG. 11 is a flowchart illustrating a method of estimating glucose exposure according to another exemplary embodiment.

FIG. 11 is a flowchart illustrating a method of estimating glucose exposure according to another exemplary embodiment. The method of FIG. 11 may be performed by the apparatus 100 of FIG. 1 for estimating glucose exposure. Here, operations 1110, 1120, and 1130 are substantially the same as operations 910, 920, and 930, and thus detailed descriptions thereof will not be reiterated.

In operation 1140, the apparatus 100 for estimating glucose exposure generates carbohydrate intake guide information indicating whether or not a daily amount of carbohydrate intake of an object is adequate based on the glucose exposure estimated in operation 1130. For example, the apparatus 100 may calculate a daily glucose exposure by monitoring the glucose exposure of the object and determine whether the calculated daily glucose exposure is within a predetermined threshold range. In addition, when the calculated daily glucose exposure is within the predetermined threshold range, the apparatus 100 may determine that the carbohydrate intake of the object is adequate, and when the calculated daily glucose exposure is less than the predetermined threshold range, determine that the carbohydrate intake is insufficient. In addition, when the calculated daily glucose exposure is greater than the predetermined threshold range, the apparatus 100 may determine that the carbohydrate intake is excessive. The apparatus 100 may generate carbohydrate intake guide information indicating whether the daily amount of carbohydrate intake of the object is adequate based on the determination.

Figure 12:
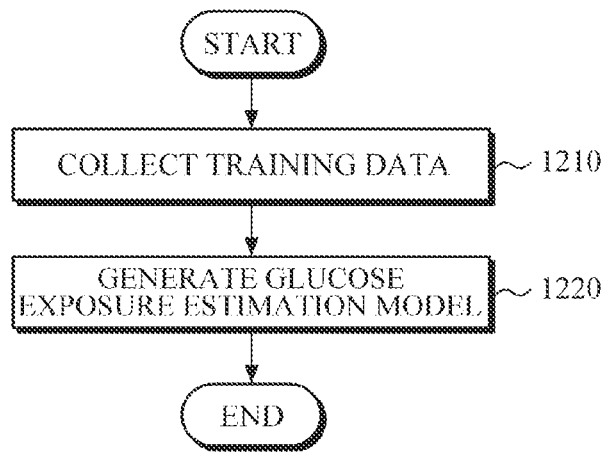
FIG. 12 is a flowchart illustrating a method of generating a glucose exposure estimation model according to one exemplary embodiment.

FIG. 12 is a flowchart illustrating a method of generating a glucose exposure estimation model according to one exemplary embodiment. The method of FIG. 12 may be performed by the apparatus 700 of FIG. 7 for generating a glucose exposure estimation model.

Referring to FIGS. 7 and 12, the apparatus 700 for generating a glucose exposure estimation model collects a Raman spectrum and glucose exposure information corresponding to the Raman spectrum as training data. In this case, the Raman spectrum collected as the training data may be a plurality of Raman spectra measured at a predetermined time interval for a predetermined period of time, or may be a representative Raman spectrum extracted from the plurality of Raman spectra. In addition, the Raman spectrum collected as the training data may be raw data from which noise has not been removed, or data from which noise has been removed.

The apparatus 700 may extract depth-specific protein information from the collected Raman spectrum and generate a glucose exposure estimation model based on the extracted depth-specific protein information and glucose exposure information corresponding to the Raman spectrum data. The processor 720 may obtain the glucose exposure information by calculating an area under a blood glucose response curve that is measured for two hours after food is consumed. The depth-specific protein information may include intradermal collagen information and intraepidermal keratin information. For example, the apparatus 700 may extract a first Raman peak value as the intradermal collagen information and a second Raman peak value as the intraepidermal keratin information from the Raman spectrum. In addition, the apparatus 700 may generate the glucose exposure estimation model through regression analysis or machine learning using a ratio of the first Raman peak value and the second Raman peak value and the corresponding glucose exposure data.

Meanwhile, the apparatus 700 may perform various preprocessing operations according to the collected Raman spectrum. For example, when the collected Raman spectrum is raw data, the apparatus 700 may remove simple additive noise and/or background noise from the Raman spectrum data. In addition, when the collected data is a plurality of Raman spectra measured at the predetermined time interval for the predetermined period of time, the apparatus 700 may extract a representative Raman spectrum from the plurality of Raman spectra.

Figure 13:
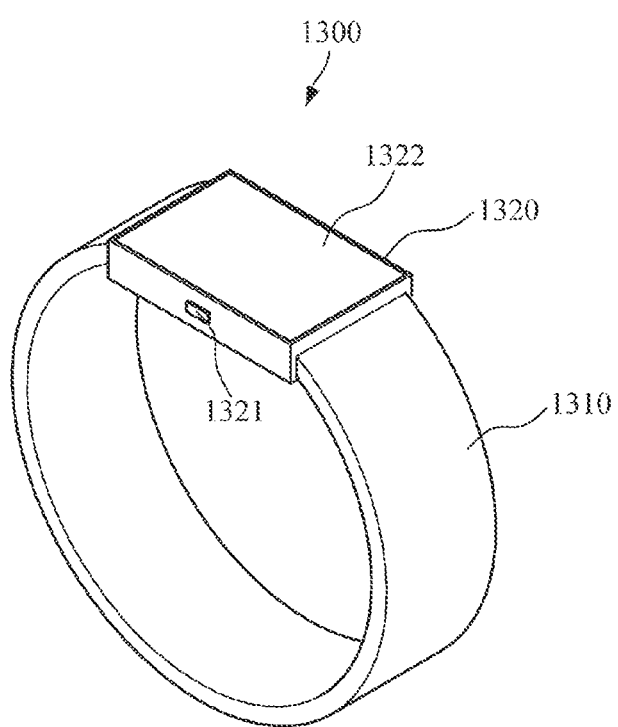
FIG. 13 is a perspective view of a wrist wearable device.

FIG. 13 is a perspective view of a wrist wearable device.

Referring to FIG. 13, the wrist wearable device 1300 includes a strap 1310 and a main body 1320.

The strap 1310 may be configured in the form of a flexible band, but this is merely an example, and aspects of the present disclosure are not limited thereto. That is, the strap 1310 may be configured with a plurality of strap members formed to be bent to surround a wrist of a user.

The above-described apparatus 100 or 600 for estimating glucose exposure and/or the apparatus 700 for generating a glucose exposure estimation model may be mounted in the main body 1320. In addition, a battery may be embedded in the main body 1320 to supply power to the wrist wearable device 1300, the apparatus 100 or 600 for estimating glucose exposure, and the apparatus 700 for generating a glucose exposure estimation model.

The wrist wearable device 1300 may further include an input interface 1321 and a display 1322 which are mounted in the main body 1320. The input interface 1321 may receive various operation signals from the user. The display 1322 may display data processed by the wrist wearable device 1300, the apparatus 100 or 600 for estimating glucose exposure and the apparatus 700 for generating a glucose exposure estimation model and processing result data.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating a glucose exposure, the apparatus comprising:
    a spectrometer configured to measure a plurality of Raman spectra from an object; and
    a processor configured to extract depth-specific protein information from the plurality of Raman spectra and estimate the glucose exposure of the object based on the depth-specific protein information,
    wherein the processor is further configured to extract a representative Raman spectrum from the plurality of Raman spectra and extract the depth-specific protein information from the representative Raman spectrum, and
    wherein the processor is further configured to extract a Raman spectrum of a predetermined sample number from the plurality of Raman spectra as the representative Raman spectrum.

2. The apparatus of claim 1, wherein the spectrometer comprises:
    a light source configured to emit a light to the object; and
    a photodetector configured to acquire the plurality of Raman spectra by receiving the light reflected or scattered from the object.

3. The apparatus of claim 1, wherein the spectrometer is further configured to measure the plurality of Raman spectra at a predetermined time interval for a predetermined period of time.

4. The apparatus of claim 1, wherein the processor is further configured to remove background noise from the extracted representative Raman spectrum.

5. The apparatus of claim 1, wherein the depth-specific protein information comprises intradermal collagen information and intraepidermal keratin information.

6. The apparatus of claim 1, wherein the processor is further configured to extract a first Raman peak value corresponding to intradermal collagen information and a second Raman peak value corresponding to intraepidermal keratin information from the plurality of Raman spectra, and estimate the glucose exposure of the object based on the first Raman peak value, the second Raman peak value, and a glucose exposure estimation model.

7. The apparatus of claim 6, wherein the glucose exposure estimation model defines a relationship between the glucose exposure and a ratio of the first Raman peak value to the second Raman peak value.

8. The apparatus of claim 1, wherein the processor is further configured to generate carbohydrate intake guide information based on the glucose exposure of the object.

9. The apparatus of claim 8, wherein the carbohydrate intake guide information comprises information indicating whether a daily amount of carbohydrate intake of the object is adequate.

10. The apparatus of claim 8, wherein the processor is further configured to determine a daily amount of the glucose exposure by monitoring the glucose exposure of the object, determine whether the calculated daily amount of the glucose exposure is within a predetermined threshold range, and generate the carbohydrate guide information based on a result of a determination of whether the calculated daily amount is within the predetermined threshold range.

* * * * *